US00PP22749P3

(12) United States Plant Patent
Bartels

(10) Patent No.: US PP22,749 P3
(45) Date of Patent: May 22, 2012

(54) ***PHLOX* PLANT NAMED 'BARSIXTYFIVE'**

(50) Latin Name: *Phlox paniculata*
Varietal Denomination: Barsixtyfive

(75) Inventor: Gosen B. H. Bartels, Aalsmeer (NL)

(73) Assignee: Bartels Breeding B.V., Aalsmeer (NL)

( * ) Notice: Subject to any disclaimer, the term of this patent is extended or adjusted under 35 U.S.C. 154(b) by 32 days.

(21) Appl. No.: 12/802,687

(22) Filed: Jun. 11, 2010

(65) Prior Publication Data

US 2011/0307986 P1 Dec. 15, 2011

(51) Int. Cl.
*A01H 5/00* (2006.01)

(52) U.S. Cl. ..... Plt./320

(58) Field of Classification Search ..... Plt./320
See application file for complete search history.

(56) References Cited

U.S. PATENT DOCUMENTS

PP11,804 P2 * 3/2001 Bartels ..... Plt./320

* cited by examiner

*Primary Examiner* — June Hwu

(74) *Attorney, Agent, or Firm* — Jondle & Associates, P.C.

(57) ABSTRACT

A new *Phlox paniculata* plant particularly distinguished by a vigorous growth habit and violet inflorescences with pink eyes, is disclosed.

2 Drawing Sheets

Genus and species: *Phlox paniculata.*
Variety denomination: 'Barsixtyfive'.

BACKGROUND OF THE NEW PLANT

The present invention comprises a new and distinct variety botanically known as *Phlox paniculata,* and hereinafter referred to by the variety name 'Barsixtyfive'. The new variety originated from an open pollination made in 2004 in Aalsmeer, The Netherlands. The female parent was the proprietary *Phlox paniculata* plant '03-18-06' (unpatented), while the male parent was an unknown *Phlox paniculata* plant (unpatented).

'Barsixtyfive' was first propagated by vegetative cuttings in 2004 in Aalsmeer, The Netherlands and has been subsequently asexually propagated by vegetative cuttings in Aalsmeer, The Netherlands since 2004. The present invention has been found to retain its distinctive characteristics through successive asexual propagations via vegetative cuttings.

Plant Breeder's Rights for this variety were applied for in May 2010 for Europe. 'Barsixtyfive' has not been made publicly available or sold more than one year prior to the filing date of this application.

SUMMARY OF THE INVENTION

The following are the most outstanding and distinguishing characteristics of this new variety when grown under normal horticultural practices in Aalsmeer, The Netherlands.

1. A vigorous growth habit; and
2. Violet inflorescences with pink eyes.

DESCRIPTION OF THE PHOTOGRAPHS

This *Phlox paniculata* plant is illustrated by the accompanying photographs which show the overall plant habit including blooms, buds, and foliage of the plant. The colors shown are as true as can be reasonably obtained by conventional photographic procedures.

Figure 1:
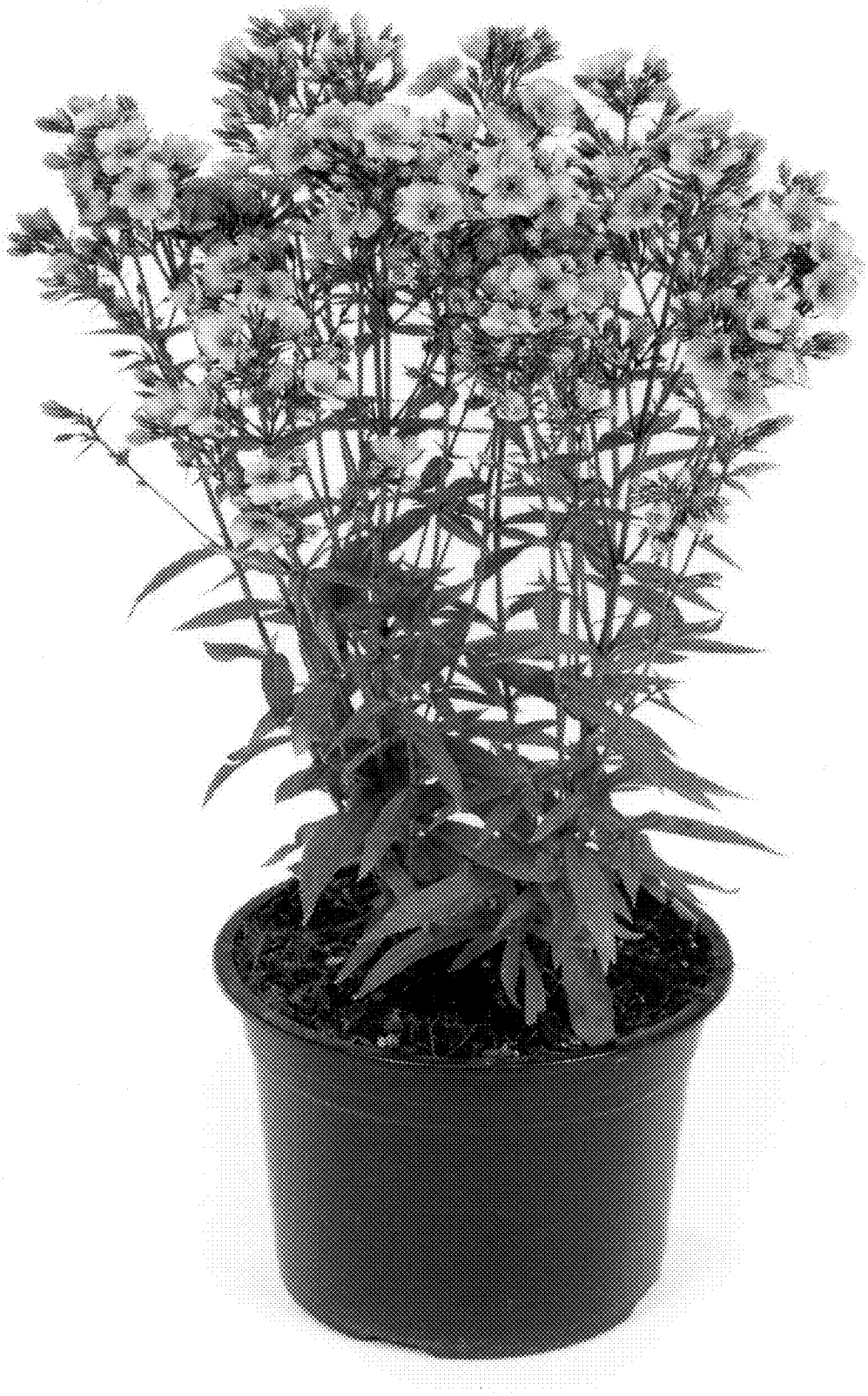
Figure 2:
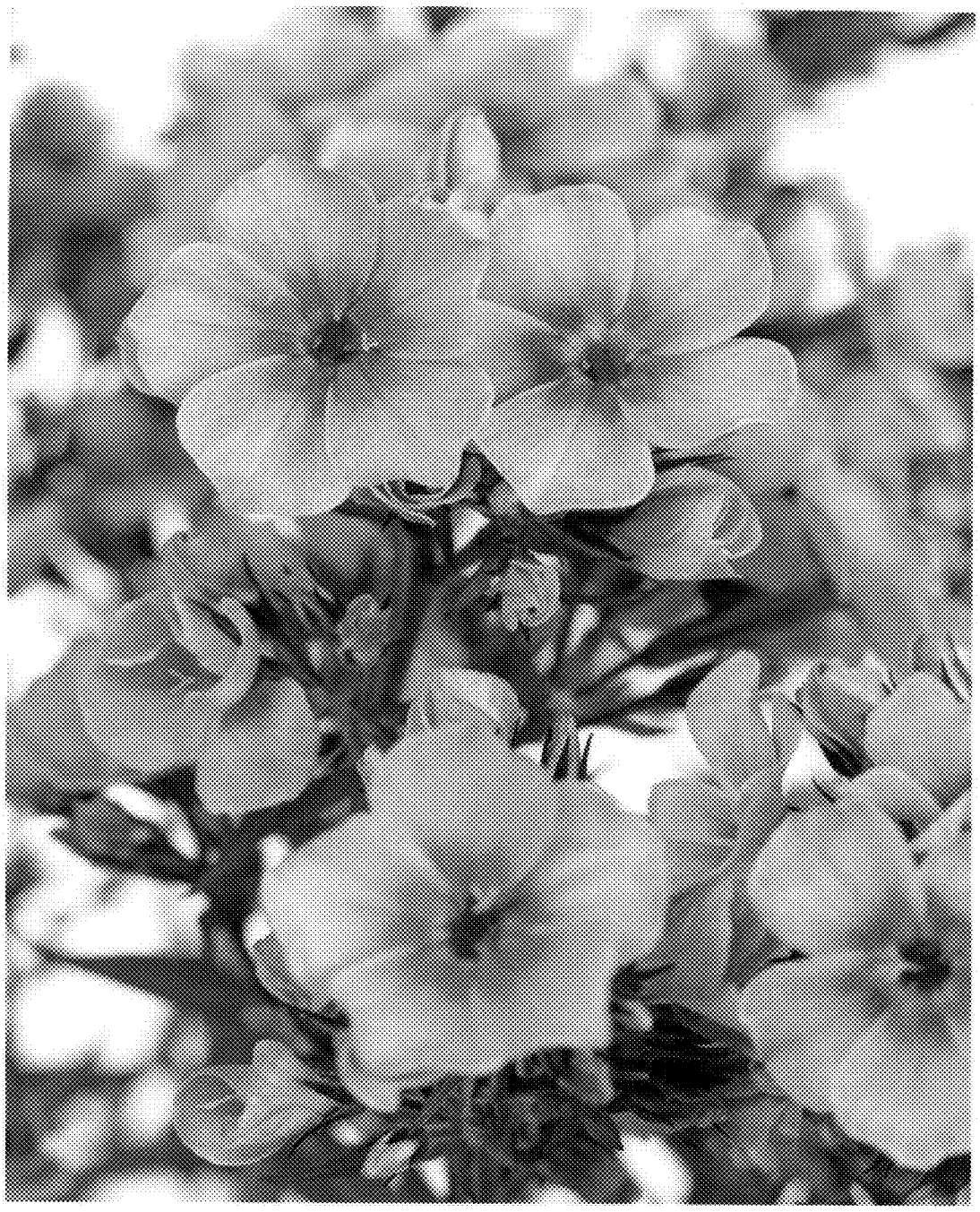

FIG. 1 shows the overall plant habit.
FIG. 2 shows a close-up of an inflorescence.

DESCRIPTION OF THE NEW VARIETY

The following detailed description sets forth the distinctive characteristics of 'Barsixtyfive'. The data which defines these characteristics were collected from asexual reproductions carried out in Aalsmeer, The Netherlands in spring/early summer 2010. Color readings were taken under natural light outdoors. Color references are primarily to The R.H.S. Colour Chart of The Royal Horticultural Society of London (R.H.S.) (2001).

DETAILED BOTANICAL DESCRIPTION

Classification:
- *Family.*—Polemoniaceae.
- *Botanical name.*—*Phlox paniculata.*
- *Common name.*—*Phlox.*
- *Denomination.*—'Barsixtyfive'.

Plant:
- *Growth habit.*—Vigorous.
- *Form.*—Narrow, bushy.
- *Habit.*—Upright.
- *Height* (*measured from the top of the soil*).—30.0 cm to 40.0 cm.
- *Diameter or area of spread.*—30.0 cm.
- *Propagation.*—Via vegetative cuttings.
- *Time to produce a finished flowering plant.*—4 months.
- *Lastingness of inflorescence on the plant.*—4 weeks.
- *Outdoor plant performance.*—Very good.
- *Time to initiate and develop roots.*—2 weeks.
- *Time to produce a rooted cutting or liner* (*young plant*).—5 weeks.
- *Root description.*—White fibrous.

Branches:
- *Number of branches per plant.*—5.
- *Length of lateral branches.*—35.0 cm.

*Diameter of a cluster of lateral branches.*—15.0 cm.
*Texture*.—Smooth.

Stems:
*Shape in cross-section.*—Circular.
*Aspect*.—Smooth.
*Color*.—RHS 143C.
*Diameter.*—5.0 mm to 8.0 mm.
*Length.*—40.0 cm.
*Internode length.*—2.0 cm to 3.0 cm.
*Anthocyanin*.—Present; RHS 187A.
*Pubescence*.—Present, but in low density.

Leaves:
*Arrangement*.—Alternate.
*Quantity of leaves* (*per lateral branch*).—26 to 30.
*Apex*.—Acute.
*Base*.—Rounded.
*Color* (*mature and immature leaves*).—Upper surface: RHS 137A. Lower surface: RHS 137B.
*Margin*.—Smooth.
*Texture* (*both upper and lower surfaces*).—Smooth.
*Length.*—8.0 cm.
*Width.*—3.0 cm.
*Shape*.—Lanceolate.
*Pubescence* (*both upper and lower surfaces*).—Absent.
*Venation type*.—Featherlike.
*Venation color*.—RHS 144B.
*Petiole*.—Color: RHS 144B. Length: 2.0 mm. Diameter: 3.0 mm. Texture: Smooth.

Flower buds:
*Color*.—RHS 73A.
*Shape*.—Oblong.
*Length.*—2.0 cm.
*Diameter.*—6.0 mm.

Inflorescence:
*Blooming habit*.—Flattened panicle.
*Inflorescence type*.—Terminal panicle.
*Arrangement*.—Terminal and lateral.
*Quantity of flowers per inflorescence.*—50 to 70.
*Quantity of flowers and buds per plant*.—Greater than 100.
*Height.*—15.0 cm.
*Width.*—15.0 cm.
*Shape*.—Globe to flat shaped.
*Fragrance*.—Present.
*Peduncle*.—Color: RHS 144B. Length: 15.0 cm. Diameter: 15.0 mm. Texture: Smooth. Pubescence: Absent.
*Pedicel*.—Color: RHS 138C. Length: 1.0 cm. Diameter: 0.2 cm. Texture: Smooth.

Flowers:
*Flower type*.—Actinomorphic.
*Height* (*flower depth*).—1.5 cm.
*Diameter.*—1.5 cm.
*Flower tube length.*—1.5 cm.
*Throat diameter.*—3.0 mm to 4.0 mm.
*Color of flower throat*.—RHS 67A.
*Texture* (*both upper and lower surfaces*).—Smooth.
*Corolla*.—Shape: Circular. Color: Inside: RHS 73B and RHS N66A. Outside: RHS 75C. Length: 1.5 cm. Diameter: 1.5 cm.
*Petals*.—Arrangement: Single whorl. Lobe shape: Rotundate to cuspidate. Quantity per flower: 5. Length (from the throat): 0.7 cm. Width: 0.7 cm. Apex: Obcordate. Base: Fused. Margin: Smooth. Color (when opening): Upper surface: RHS 73B and RHS N66A. Lower surface: RHS 75C. Color (fully opened): Upper surface: RHS 73B and RHS N66A. Lower surface: RHS 75C fading to RHS 75D. Pubescence (both upper and lower surfaces): Absent.
*Calyx*.—Shape: Funnel. Length: 8.0 mm. Diameter 3.0 mm.
*Sepals*.—Arrangement: Single whorl. Quantity per flower: 5. Shape: Narrow triangular. Apex: Pointed. Base: Fused. Margin: Smooth. Length: 6.0 mm. Width: 2.0 mm. Texture (both upper and lower surfaces): Smooth. Color (mature; both surfaces): RHS 147A. Color (immature; both surfaces): RHS 143C.

Reproductive organs:
*Quantity of stamens* (*per flower*).—5.
*Anther*.—Shape: Linear. Length: 0.2 cm. Color: RHS 8C.
*Filament Color*.—RHS 62D.
*Pollen amount*.—Absent to few.
*Pollen color*.—RHS 19B.
*Pistil*.—Quantity (per flower): 1. Length: 20.0 mm.
*Style*.—Length: 18.0 mm. Color: RHS 143C.
*Stigma*.—Shape: 3 lobes. Color: RHS 143D.
*Ovary Color*.—RHS 143A.

Seed: None observed.

Disease and pest resistance: Tolerant to powdery mildew.

COMPARISON WITH COMMERCIAL VARIETY

'Barsixtyfive' differs from the commercial variety 'Bareleven' (U.S. Plant Pat. No. 11,805) in that 'Barsixtyfive' has a flattened raceme-like flowering canopy, smaller-sized flowers (1.5 cm), and an earlier flowering time, while 'Bareleven' has a raceme-like flowering canopy, larger-sized flowers (3.0 cm), and the flowering time is two to three weeks later than 'Barsixtyfive'.

I claim:

1. A new and distinct variety of *Phlox paniculata* plant as described and shown herein.

* * * * *